United States Patent
Versaggi et al.

(10) Patent No.: US 9,623,110 B2
(45) Date of Patent: *Apr. 18, 2017

(54) NANOPARTICLES OF A METAL AND A NUCLEOBASE

(71) Applicant: CERION, LLC, Rochester, NY (US)

(72) Inventors: Ashley Renée Versaggi, Scottsville, NY (US); Wendi Ann Costanzo, Webster, NY (US); Kenneth Joseph Reed, Brighton, NY (US)

(73) Assignee: CERION, LLC, Rochester, NY (US)

( * ) Notice: Subject to any disclaimer, the term of this patent is extended or adjusted under 35 U.S.C. 154(b) by 52 days.

This patent is subject to a terminal disclaimer.

(21) Appl. No.: 14/456,197

(22) Filed: Aug. 11, 2014

(65) Prior Publication Data

US 2015/0045450 A1 Feb. 12, 2015

Related U.S. Application Data

(60) Provisional application No. 61/958,943, filed on Aug. 9, 2013.

(51) Int. Cl.
| | |
|---|---|
| *A61K 47/48* | (2006.01) |
| *A61K 9/10* | (2006.01) |
| *A61K 47/22* | (2006.01) |
| *A61K 47/02* | (2006.01) |
| *A61K 51/12* | (2006.01) |

(52) U.S. Cl.
CPC .......... *A61K 47/02* (2013.01); *A61K 51/1251* (2013.01)

(58) Field of Classification Search
None
See application file for complete search history.

(56) References Cited

U.S. PATENT DOCUMENTS

| | | | |
|---|---|---|---|
| 7,534,453 B1 | 5/2009 | Rzigalinski et al. | |
| 2005/0142567 A1* | 6/2005 | Su | G01N 21/6428 435/6.11 |

FOREIGN PATENT DOCUMENTS

| | | |
|---|---|---|
| WO | WO 2007/002662 | 1/2007 |
| WO | WO 2008/002323 | 1/2008 |
| WO | WO 2008/030815 | 3/2008 |

OTHER PUBLICATIONS

Ghosh et al. in Journal of Polymer Science 17, 2119-2127 (1979).*
Rzigalinski, Beverly A. Ph.D., "Nanoparticles and Cell Longevity," Technology in Cancer Research and Treatment, vol. 4, No. 6, pp. 651-659, Dec. 2005.
Masui, T. et al., "Synthesis of Cerium Oxide Nanoparticles by Hydrothermal Crystallization With Citric Acid," J. Mater. Sci. Lett. 21, pp. 489-491, 2002.
Hardas, Sarita et al., "Brain Distribution and Toxicological Evaluation of a Systemically Delivered Engineered Nanoscale Ceria," Toxicologial Sciences 116(2), pp. 562-576, 2010.
Karokoti, A.S. et al.; "Direct Synthesis of Nanoceria in Aqueous Polyhydroxyl Solutions," J. Physical Chem. C 111, pp. 17232-17240, 2007.
Karokoti, A.S. et al., "Nanoceria as Antioxidant: Systhesis and Biomedical Applications," Journal of the Minerals, Metals & Materials Society (JOM), 60(2), pp. 33-37, Mar. 2008.
Robert A. Yokel et al. "Biodistribution and Oxidative Stress Effects of a Systemically-Introduced Commercial Ceria Engineered Nanomaterial," Nanotoxicology, vol. 3, pp. 234-248, Sep. 2009.

* cited by examiner

*Primary Examiner* — Dennis Heyer
(74) *Attorney, Agent, or Firm* — RatnerPrestia

(57) ABSTRACT

A process for making nanoparticles of biocompatible materials is described, wherein an aqueous reaction mixture comprising a metal ion, a nucleobase, an oxidant, and water, is provided along with temperature conditions to directly form within the reaction mixture, a stable dispersion of nanoparticles. Biocompatible nanoparticles comprised of cerium or iron as the metal ion, and a purine and/or a pyrimidine as the nucleobase, are described.

12 Claims, 2 Drawing Sheets

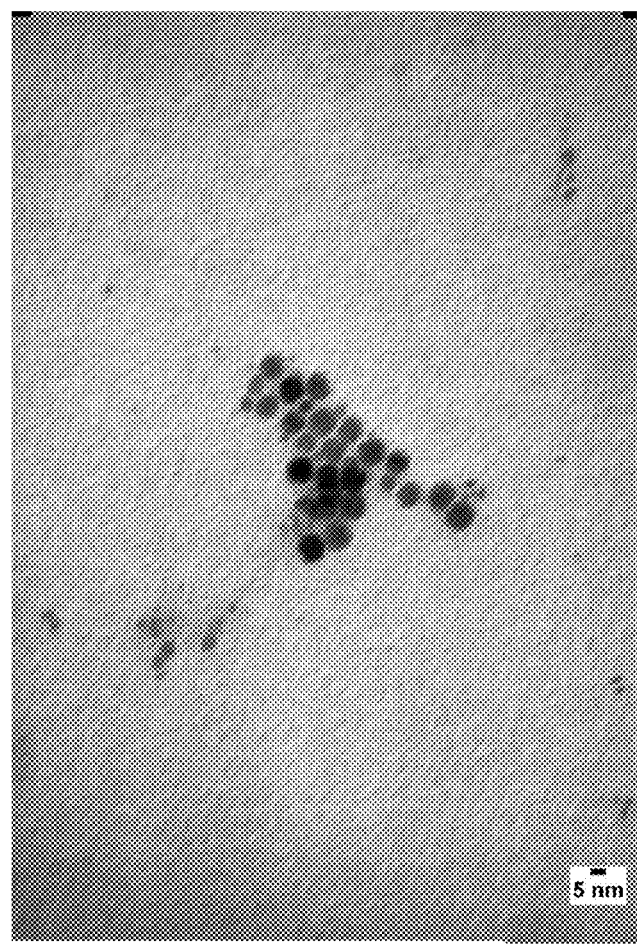
FIG. 1: TEM image of Nanoparticles Prepared with 0.4/1.0 Uracil/Cerium

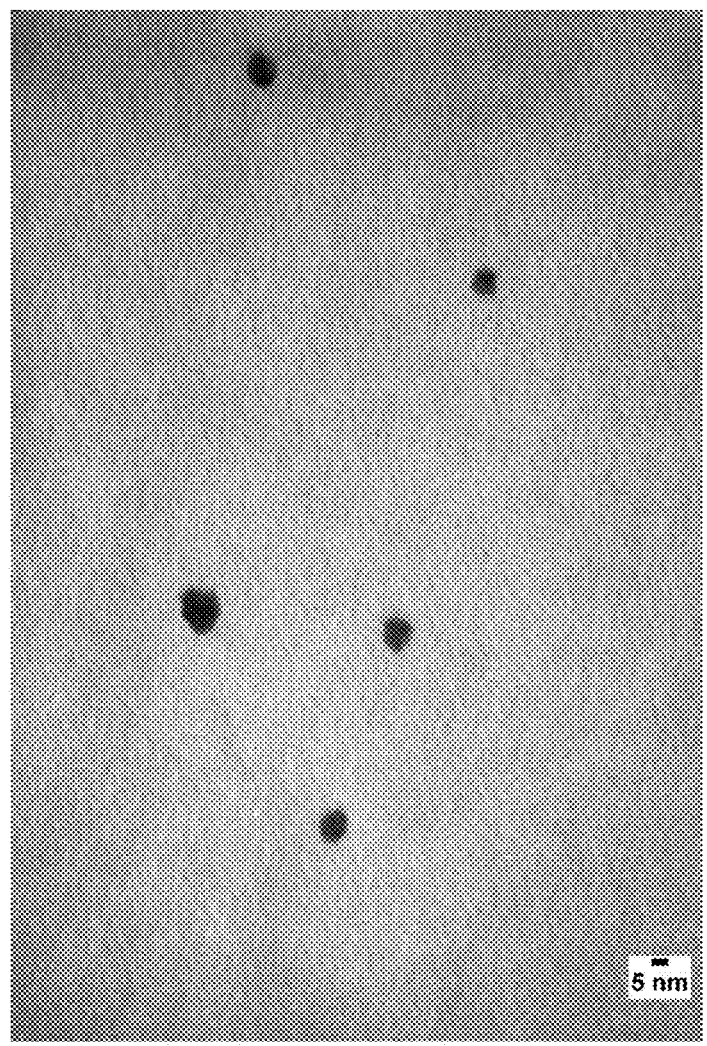
FIG. 2: TEM image of the particles prepared with 0.4/1.0 (Adenine and Thymine)/Cerium

NANOPARTICLES OF A METAL AND A NUCLEOBASE

CROSS-REFERENCE TO RELATED APPLICATIONS

This patent application claims the benefit of Provisional Application Ser. No. 61/958,943, NANOPARTICLES OF A METAL AND A NUCLEOBASE, filed Aug. 9, 2013, the disclosure of which is incorporated herein by reference in its entirety.

FIELD OF THE INVENTION

The present invention relates in general to improvements in the fields of nanoscience and nanomedicine. In particular, the invention relates to nanoparticles prepared with biocompatible materials, to methods of preparing such nanoparticles, and to the use of such nanoparticles to treat disease.

BACKGROUND OF THE INVENTION

The origin of the use of nanoceria in nanomedicine can be traced to the seminal work of Bailey and Rzigalinski, wherein the application of ultrafine cerium oxide particles to brain cells in culture was observed to greatly enhanced cell survivability, as described by Rzigalinski in Nanoparticles and Cell Longevity, *Technology in Cancer Research & Treatment* 4(6), 651-659 (2005). More particularly, rat brain cell cultures in vitro were shown to survive approximately 3-4 times longer when treated with 2-10 nanometer (nm) sized cerium oxide nanoparticles synthesized by a reverse micelle micro emulsion technique, as disclosed by Rzigalinski et al. in U.S. Pat. No. 7,534,453, filed Sep. 4, 2003. Cultured brain cells exposed to a lethal dose of free radicals generated by hydrogen peroxide or ultraviolet light exposures were afforded considerable protection by the cerium oxide nanoparticles. In addition, the cerium oxide nanoparticles were reported to be relatively inert in the murine body, with low toxicity (e.g. tail vein injections produced no toxic effects). While no in vivo medical benefits were reported, benefits were postulated for treatments with these ceria nanoparticles, including reduced inflammation associated with wounds, implants, arthritis, joint disease, vascular disease, tissue aging, stroke and traumatic brain injury.

However, a host of problems with these particular nanoceria particles was subsequently disclosed by Rzigalinski et al. in WO 2007/002662. Nanoceria produced by this reverse micelle micro emulsion technique suffered from several problems: (1) particle size was not well-controlled within the reported 2-10 nanometer (nm) range, making variability between batches high; (2) tailing of surfactants, such as sodium bis(ethylhexyl)sulphosuccinate, also known as docusate sodium or (AOT), used in the process into the final product caused toxic responses; (3) inability to control the amount of surfactant tailing posed problems with agglomeration when these nanoparticles were placed in biological media, resulting in reduced efficacy and deliverability; and (4) instability of the valence state of cerium (+3/+4) over time. Thus, the cerium oxide nanoparticles produced by the reverse micelle micro emulsion technique were highly variable from batch to batch, and showed higher than desired toxicity to mammalian cells.

As an alternative, Rzigalinski et al. in WO 2007/002662 describe the biological efficacy of nanoceria synthesized by high temperature techniques, obtained from at least three commercial sources. These new sources of cerium oxide nanoparticles were reported to provide superior reproducibility of activity from batch to batch. It was further reported that, regardless of source, cerium oxide particles having a small size, narrow size distribution, and low agglomeration rate are most advantageous. In regard to size, this disclosure specifically teaches that in embodiments where particles are taken into the interior of cells, the preferable size range of particles that are taken into the cell are from about 11 nm to about 50 nm, such as about 20 nm. In embodiments where particles exert their effects on cells from outside the cells, the preferable size range of these extracellular particles is from about 11 nm to about 500 nm.

These inventors (Rzigalinski et al.) also report that for delivery, the nanoparticles were advantageously in a non-agglomerated form. To accomplish this, they reported that stock solutions of about 10% by weight could be sonicated in ultra-high purity water or in normal saline prepared with ultra-high purity water. However, we have confirmed what others have observed, that sonicated aqueous dispersions of nanoceria (synthesized by high temperature techniques and obtained from commercial sources) are highly unstable, and settle rapidly (i.e. within minutes), causing substantial variability in administering aqueous dispersions of nanoceria derived from these sources.

Yokel et al. in *Nanotoxicology*, 2009, 3(3): 234-248, describe an extensive study of the biodistribution and oxidative stress effects of a commercial ceria nanomaterial. In particular, a 5% nanoceria dispersion obtained from Aldrich (#639648) was sonicated for 3 minutes and infused into rats at 50, 250 and 750 mg/kg nanoceria dose. The nature of any nanoparticle surface stabilizer(s) was unknown for this material. The size of the nanoceria particles was characterized by a variety of techniques and reported to be on average 31+/−4 nm by dynamic light scattering. Transmission electron microscopy (TEM) revealed that most of the particles were platelets with a bimodal size distribution with peaks at 8 nm and 24 nm, along with some particles ~100 nm. It was observed that blood incubated for 1 hour with this form of nanoceria had agglomerates ranging from ~200 nm to greater than 1 micron, and that when infused into rats, it was rapidly cleared from the blood (half-life of 7.5 minutes). Most of the nanoceria was observed to accumulate in the liver and spleen, while it was not clear that any substantial amount had penetrated the blood brain barrier and entered brain tissue cells.

This group of authors then sought precise control over the nanoceria surface coating (stabilizer) and prepared stable aqueous dispersions of nanoceria by the direct two-step hydrothermal preparation of Masui et al., *J. Mater. Sci. Lett.* 21, 489-491 (2002), which included sodium citrate as a biocompatible stabilizer. High resolution TEM revealed that this form of nanoceria possessed crystalline polyhedral particle morphology with sharp edges. Citrate stabilized dispersions of these 5 nm average ceria nanoparticles were reported to be stable for more than 2 months at a physiological pH of 7.35 and zeta potential of −53 mV. Thus no sonication prior to administration was required.

Results of an extensive biodistribution and toxicology study of this form of citrate stabilized nanoceria was reported by this group of authors in Hardas et al., *Toxicological Sciences* 116(2), 562-576 (2010). Surprisingly, they report that compared with the previously studied ~30 nm nanoceria (Aldrich (#639648) described above), this nanoceria was more toxic, was not seen in the brain, and had little influence on degree of oxidative stress in the hippocampus and cerebellum. The results were contrary to the hypothesis that smaller engineered nanomaterial would readily permeate the blood brain barrier.

While cerium oxide containing nanoparticles can be prepared by a variety of techniques known in the art, the particles typically require a stabilizer to prevent undesirable agglomeration. In regard to biocompatible nanoceria stabilizers used previously, once again, Masui et al., *J. Mater. Sci. Lett.* 21, 489-491 (2002) describe a two-step hydrothermal process that directly produces stable aqueous dispersions of ceria nanoparticles that use citrate buffer as a stabilizer. However, this process is both time and equipment intensive, requiring two separate 24 hours reaction steps in closed reactors.

Sandford et al., WO 2008/002323 A2, describe an aqueous preparation technique using a biocompatible stabilizer (acetic acid) that directly produces nanoparticle dispersions of cerium dioxide without precipitation and subsequent calcination. Cerous ion is slowly oxidized to ceric ion by nitrate ion, and a stable non-agglomerated sol of 11 nm crystallite size (and approximately equal grain size) is obtained when acetic acid is used as a stabilizer.

DiFrancesco et al. in PCT/US2007/077545, METHOD OF PREPARING CERIUM DIOXIDE NANOPARTICLES, filed Sep. 4, 2007, describes the oxidation of cerous ion by hydrogen peroxide at low pH (<4.5) in the presence of biocompatible stabilizers, such as citric acid, lactic acid, tartaric acid, ethylenediaminetetraacetic acid (EDTA), and combinations thereof. Specifically, the stabilizer lactic acid and the combination of lactic acid and EDTA are shown to directly produce stable dispersions of nanoceria.

Karakoti et al. in *J. Phys. Chem. C* 111, 17232-17240 (2007) describe the direct synthesis of nanoceria in mono/polysaccharides by oxidation of cerous ion in both acidic conditions (by hydrogen peroxide) and basic conditions (by ammonium hydroxide). The specific biocompatible stabilizers disclosed include glucose and dextran.

Karakoti et al. in JOM (Journal of the Minerals, Metals & Materials Society) 60(3), 33-37 (2008) comment on the challenge of synthesizing stable dispersions of nanoceria in biologically relevant media, so as to be compatible with organism physiology, as requiring an understanding of colloidal chemistry (zeta potential, particle size, dispersant, pH of solution, etc.) so as not to interfere with the reduction/oxidation (redox) ability of the nanoceria that enables the scavenging of free radicals (reactive oxygen species (ROS) and reactive nitrogen species). These authors specifically describe the oxidation of cerium nitrate by hydrogen peroxide at low pH (<3.5) in the absence of any stabilizer, as well as, in the presence of dextran, ethylene glycol and polyethylene glycol (PEG) stabilizers.

The term transfection refers to a process of deliberately introducing nucleic acids into cells. However, currently available techniques for transfecting a cell are greatly limited in their ability to efficiently introduce nucleic acids into cells for the study of gene function (e.g. overexpression of genes by plasmid or gene silencing via small RNAs). The state of the art techniques in use today also suffer from issues with cytotoxicity, inefficient delivery to cells, or inability to transfect a wide range of cell lines.

As described above, various methods and apparatus have been reported for preparing dispersions of cerium-containing nanoparticles. However, a need remains for further improvements in methods for the direct preparation of biocompatible dispersions of nanoparticles, for example, without isolation and redispersal of the nanoparticles, in a shorter period of time and at higher suspension densities, that are sufficiently small in size (e.g. sufficiently small in size to evade detection by an immune system), stable and non-toxic in a wide range of biological media. Additionally, it would be quite useful to produce these nanoparticles and conjugates thereof with zeta potentials whose magnitude could be varied at will over a relatively large range. Finally, it would be very desirable to produce biocompatible stabilized nanoparticles that can effectively form conjugates with other biologically active agents, such as, for example, peptides/proteins, segments of RNA and DNA, for use as transfection agents.

SUMMARY OF THE INVENTION

In accordance with a first aspect the invention, a process of making a dispersion of nanoparticles is provided, comprising: forming a reaction mixture comprising a metal ion, a nucleobase, an oxidant, and water; optionally, heating or cooling the reaction mixture, and forming in the reaction mixture a dispersion of nanoparticles.

In a second aspect of the invention, a process of making a dispersion of nanoparticles is provided, comprising: forming a reaction mixture comprising cerous ion, a nucleobase, an oxidant, and water; optionally, heating or cooling the reaction mixture, and thereby directly forming in the reaction mixture, without isolation of the nanoparticles, a dispersion of cerium-containing nanoparticles.

In a third aspect of the invention, a process of making a dispersion of nanoparticles is provided, comprising: forming a reaction mixture comprising an iron ion, a nucleobase, an oxidant, and water; optionally, heating or cooling the reaction mixture, and thereby directly forming in the reaction mixture, without isolation of the nanoparticles, a dispersion of iron-containing nanoparticles.

In a fourth aspect of the invention, a nanoparticle comprising a metal and a nucleobase is provided.

In a fifth aspect of the invention, a nanoparticle comprising cerium and a nucleobase is provided.

In a sixth aspect of the invention, a nanoparticle comprising iron and a nucleobase is provided.

BRIEF DESCRIPTION OF THE DRAWINGS

FIG. 1 is a transmission electron microscopy (TEM) image representative of the nanoparticles prepared in Example 5.

FIG. 2 is a transmission electron microscopy (TEM) image representative of the nanoparticles prepared in Example 6a.

DETAILED DESCRIPTION OF THE INVENTION

It is to be understood that elements not specifically shown or described may take various forms well known to those skilled in the art. The invention is defined by the claims.

In this application, the term nanoparticle includes particles having a mean diameter of less than 100 nm. For the purposes of this disclosure, unless otherwise stated, the diameter of a nanoparticle refers to its hydrodynamic diameter, which is the diameter determined by dynamic light scattering technique and includes molecular adsorbates and the accompanying solvation shell of the particle. Alternatively, the geometric particle diameter can be estimated by analysis of transmission electron micrographs (TEM). Alternatively, the crystallographic particle diameter can be estimated by a peak width analysis of powder X-ray diffraction (XRD) spectra by use of the Scherrer equation. In addition, for substantially monodisperse nanoparticle size distributions having geometric size in the 1-10 nm range, XRD can also reveal a very low angle scattering peak that is a direct measure of size of the scattering centers.

In this disclosure, the term "metal" in referring to elements of the Periodic Table includes all elements other than those of the following atomic numbers: 1-2, 5-10, 14-18, 33-36, 52-54, 85 and 86.

The term "transition metal" is understood to encompass the 30 chemical elements of atomic number 21 to 30, 39 to 48, 57, and 72 to 80, which are included in Periods 4, 5, 6, respectively, of the Periodic Table.

The term "rare earth metal" is understood to encompass the 14 lanthanide elements of atomic number 58 to 71, and the actinide elements of atomic number greater than 90.

The term "alkali metal" is understood to encompass the 6 chemical elements forming Group 1 of the Periodic Table, those of atomic number 3, 11, 19, 37, 55, and 87.

The term "alkaline earth metal" is understood to encompass the 6 chemical elements forming Group 2 of the Periodic Table, those of atomic number 4, 12, 20, 38, 56, and 88.

In this application, the term "crystalline" is understood to describe a material that displays at least one X-ray or electron diffraction peak (excluding low angle XRD peaks), wherein the peak intensity is discernibly greater than the background scattering (baseline noise). The terms "semi-crystalline" or "partially crystalline" are understood to describe a material that displays only broad X-ray or electron diffraction peaks of low peak intensity due to a lack of long-range order. The term "amorphous" is understood to describe a material that does not display any X-ray or electron diffraction peaks (excluding very low angle XRD peaks).

In accordance with one aspect of the invention, a process is provided comprising: forming a reaction mixture comprising a metal ion, a nucleobase, an oxidant, and water; and forming in the reaction mixture a dispersion of nanoparticles.

In a particular embodiment, the dispersion of nanoparticles is formed directly in the reaction mixture, without isolation of the nanoparticles. The terms "formed directly" and "without isolation" is understood to mean that a dispersion is formed in the reaction mixture without filtering, centrifuging, collecting, or resuspending the nanoparticles.

In a particular embodiment, the reaction mixture is heated or cooled to a temperature in the range of about 0° C. to about 100° C. In particular embodiments, the reaction mixture is heated or cooled to temperatures greater than 20° C., or less than or equal to 20° C. In various embodiments, the reaction mixture is heated or cooled to temperatures greater than about 30° C., about 40° C., about 50° C., about 60° C., about 70° C., about 80° C. or about 90° C. In a particular embodiment, the reaction mixture is heated or cooled to temperatures less than the boiling temperature of water.

In embodiments employing elevated reaction temperatures, the duration of time at elevated temperature may vary widely, for example, from minutes to hours. In particular embodiments, a reaction temperature in the range of about 40° C. to about 85° C. is maintained for a time ranging from about 10 minutes to about 4 hours.

In particular embodiments, the nanoparticles formed are dehydrated, dehydroxylated or deprotonated by heating of the reaction mixture.

In a particular embodiment, the crystallinity of the nanoparticles formed is enhanced by heating of the reaction mixture.

In various embodiments, the metal ion is a transition metal ion, rare earth metal ion, alkaline earth metal ion or an alkali metal ion. In particular embodiments, the metal ion is a cerium ion, such as a cerous ion, or an iron ion, such as a ferrous ion or a ferric ion. In other particular embodiments, the metal ion is a platinum, palladium, nickel or copper ion.

In this application, the term nucleobase refers to a molecule of the purine or pyrimidine classes of molecules. Purines are nitrogenous bases having a double-ringed aromatic structure. In particular embodiments, nucleobases of the purine class include, but are not limited to, molecules of adenine, caffeine, guanine, 7-methylguanine, isoguanine, xanthine, hypoxanthine, theobromine, purine, 2-amino-6-(2-thienyl)purine, and uric acid. Pyrimidines are nitrogenous bases having a particular single-ringed aromatic structure. In particular embodiments, nucleobases of the pyrimidine class include, but are not limited to, cytosine, 5-methylcytosine, 5-hydroxymethylcytosine, isocytosine, thymine, uracil, and 5,6-dihydrouracil. While various chemical derivatives of purine and pyrimidine molecules are, in general, contemplated herein as embodiments of a nucleobase, specifically excluded as nucleobases are segments of ribonucleic acid (RNA) and segments of deoxyribonucleic acid (DNA), as well as nucleotides and nucleosides.

In various embodiments, mixtures of purine nucleobases, mixtures of pyrimidine nucleobases, and mixtures of purine and pyrimidine nucleobases, are employed. In a particular embodiment, a mixture of purine and pyrimidine nucleobases includes adenine and thymine.

In various embodiments, the oxidant includes compounds more oxidizing than molecular oxygen (or an ambient atmosphere of air). In other embodiments, the oxidant has an aqueous half-cell reduction potential greater than −0.13 volts relative to the standard hydrogen electrode. In particular embodiments the oxidant is an alkali metal or ammonium perchlorate, chlorate, hypochlorite or persulfate; ozone, a peroxide, such as hydrogen peroxide ($H_2O_2$) or tert-butyl hydroperoxide; or a combination thereof.

In various embodiments, the amount of oxidant employed varies widely in relation to the total amount of metal ions present. In particular embodiments the molar amount of oxidant present is equal to or greater than the total molar amount of metal ions. In specific embodiments, two-electron oxidants, such as hydrogen peroxide, are present in at least one-half the molar concentration of total oxidizable metal ions, such as ferrous ion or cerous ion.

In various embodiments, the oxidant is added to the reaction mixture alone or concurrently with one or more of the other reactants.

In a particular embodiment, molecular oxygen is passed through the reaction mixture.

In particular embodiments, the pH of the reaction mixture is adjusted by the addition of an acid or base.

In various embodiments, the reaction mixture is formed in a batch reactor, a continuous reactor or a colloid mill. In two particular embodiments of a continuous reactor, a continuous-stirred-tank reactor or a plug-flow reactor are used.

The particular embodiments, various mixing devices known in the art are employed to stir, mix, shear or agitate the contents of the reaction mixture. In various embodiments, mixers comprising stir bars, marine blade propellers, pitch blade turbines or flat blade turbines are used. In particular embodiments, a colloid mill or a Silverson® High Shear Mixer is employed. In a particular embodiment, a high shear mixer that forces the reaction mixture to pass through a screen, wherein holes vary in size from fractions of a millimeter to several millimeters, is employed. In particular embodiments, one or more of the reactants is introduced below the surface of the aqueous reaction mixture. In a particular embodiment, a reactant is introduced below the surface of the aqueous reaction mixture in close proximity to a mixing device.

In various embodiments, the nanoparticles formed are amorphous, semi-crystalline or crystalline. In particular embodiments the nanoparticles formed are characterized by a cubic fluorite crystal structure. In a particular embodiment, the nanoparticles formed are characterized by a cerium oxide crystal structure. In a particular embodiment, the nanoparticles formed are characterized by an iron oxide crystal structure.

In this application, various cerium-containing materials are nominally described as a "cerium oxide" phase or "cerium dioxide" phase. It will be understood by one skilled in the chemical arts, that the actual oxidic anions present in these materials may comprise oxide anions or hydroxide anions, or mixtures thereof, such as hydrated oxide phases (e.g. oxyhydroxide). In addition, it is known that compositions of matter may be comprised of solid solutions of multivalent cations, and are termed non-stoichiometric solids. Thus, for oxide phases comprised of metal cations of multiple oxidation states, it is understood that the total amount of oxidic anions present will be determined by the specific amounts of the various oxidation states of the metal cations present (e.g. $Ce^{3+}$ and $Ce^{4+}$), such that charge neutrality is maintained. For non-stoichiometric phases nominally described as metal dioxides, this is embodied in the chemical formula $MO_{2-\delta}$, wherein the value of $\delta$ (delta) may vary. For a cerium oxide, $CeO_{2-\delta}$, the value of $\delta$ (delta) typically ranges from about 0.0 to about 0.5, the former denoting cerium (IV) oxide, $CeO_2$, the latter denoting cerium (III) oxide, $CeO_{1.5}$ (alternatively denoted $Ce_2O_3$).

Although nominally described as "iron oxide", it is generally understood by one skilled in the chemical arts, that the actual oxidic anions present may comprise oxide anions or hydroxide anions, or mixtures thereof, such as hydrated oxide phases (e.g. oxyhydroxides). There are at least 16 recognized forms of iron oxide taken in this broad sense. In the context of the present invention, the term iron oxide (for the undoped embodiments) is meant to include compounds of iron and oxygen only, or of iron, oxygen, hydrogen and water of crystallization. In general, for oxide phases comprised of metal cations of multiple oxidation states, it is understood that the total amount of oxidic anions present will be determined by the specific amounts of the various oxidation states of the metal cations present (e.g. $Fe^{2+}$ and $Fe^{3+}$), such that charge neutrality is maintained.

Some of the iron oxide phases that can be formed as a result of the inventive processes disclosed herein include, for example, FeO (Wustite), $Fe_3O_4$ (Magnetite), alpha-$Fe_2O_3$ (Hematite), gamma-$Fe_2O_3$ (Maghemite) and various hydrous ferric oxyhydroxides, such as two-line ferrihydrite ($Fe_2O_3$-$0.5H_2O$) and six-line ferrihydrite (nominally $5Fe_2O_3$-$9H_2O$), alpha-FeO(OH) (Goethite) and delta-FeO(OH).

In various embodiments, the nanoparticles formed have a hydrodynamic diameter less than 100 nm, less than 80 nm, less than 60 nm, less than 40 nm, less than 20 nm, less than 10 nm, less than 5.0 nm or less than about 2.0 nm.

In a particular embodiment of the invention, a nanoparticle comprising a metal and a nucleobase is provided.

In a particular embodiment, a nanoparticle comprising cerium and a nucleobase is provided.

In a particular embodiment, a nanoparticle comprising cerium is provided. In other embodiments, nanoparticles comprising a cerium oxide, a cerium hydroxide or a cerium oxyhydroxide are provided.

In a particular embodiment, a nanoparticle comprising a nucleobase and a cerium oxide, cerium hydroxide or cerium oxyhydroxide, is provided.

In various embodiments, the nanoparticles have a zeta potential equal to, greater than or less than zero.

In various embodiments, the zeta potential of the nanoparticle is altered by adjusting the pH, the nucleobase content, or a combination thereof, of the nanoparticle dispersion.

In a particular embodiment, the nanoparticle dispersion formed is washed to remove excess ions or by-product salts. In various embodiments, the nanoparticle dispersion is washed such that the ionic conductivity is reduced to less than about 15 millisiemens per centimeter (mS/cm), less than about 10 mS/cm, less than about 5 mS/cm or less than about 3 mS/cm. In particular embodiments, the nanoparticle dispersion formed is washed without isolation of the nanoparticles, such as, for example, by dialysis or diafiltration, thereby maintaining a stable nanoparticle dispersion.

In various embodiments, the nanoparticle dispersion formed is stable for several months, wherein no change in the visual appearance is observed.

In particular embodiments, the nanoparticle dispersions formed are concentrated to remove excess solvent or excess water. In particular embodiments, the nanoparticle dispersion is concentrated by diafiltration or centrifugation.

In various embodiments, the concentration of nanoparticles in the dispersion is greater than about 0.05 molal, greater than about 0.5 molal or greater than about 2.0 molal (approximately 35% solids in a given dispersion).

In particular embodiments, the size distributions of the nanoparticles are substantially monomodal. In other embodiments, the nanoparticle size has a coefficient of variation (COV) less than about 30%, less than about 25%, less than about 20%, less than about 15%, less than about 10% or less than about 5%, where the COV is defined as the standard deviation divided by the mean.

In various embodiments, the nanoparticles formed are used to prevent or treat a disease, such as, but not limited to, reducing complications due to inflammation, oxidative stress, radiation exposure and aging; or to transfect cells or to image cells, tissues or biological structures. In particular embodiments, the nanoparticles formed are used to prevent or treat a neurodegenerative disease, such as, but not limited to, multiple sclerosis, amyotrophic lateral sclerosis (ALS), Alzheimer's Disease, Parkinson's Disease, and Huntington's Disease. In particular embodiments, the nanoparticles formed are used to prevent or treat an oxidative stress related disease or events, such as, but not limited to, ischemic stroke, traumatic brain injury, cancer, inflammation, autoimmune disorders, lupus, inflammatory bowel disease, Crohn's Disease, ulcerative colitis, stenosis, restenosis, atherosclerosis, metabolic syndrome, endothelial dysfunction, vasospasms, diabetes, aging, chronic fatigue, coronary heart disease, cardiac fibrosis, myocardial infarction, hypertension, angina, Prizmetal's angina, ischemia, angioplasty, hypoxia, Keshan disease, glucose-6-phosphate dehydrogenase deficiency, favism, ischemic reperfusion injury, rheumatoid and osteo-arthritis, asthma, chronic obstructive pulmonary disease (e.g. emphysema and bronchitis), allergies, acute respiratory distress syndrome, chronic kidney disease, renal graft, nephritis, ionizing radiation damage, sunburn, dermatitis, melanoma, psoriasis, macular degeneration, retinal degeneration, and cataractogenesis, among others.

In one embodiment of the invention, a process of solvent shifting the aqueous nanoparticle dispersion to a less polar solvent composition by methods disclosed in commonly assigned U.S. Pat. No. 8,679,344, the disclosure of which is hereby incorporated by reference, is employed. In a specific embodiment, the nanoparticle dispersion is passed through a diafiltration column along with the addition of an organic diluent. In a specific embodiment, the organic diluent comprises one or more alcohols or glycol ethers.

In a particular embodiment of the invention, a conjugate comprising (1) a nanoparticle comprising a metal, such as, for example, cerium or iron, and a nucleobase, and (2) a biologically active agent is provided.

As used herein, the term "biologically active agent" is understood to encompass naturally occurring or synthetic agents having a biologic function, such as, for example, deoxyribonucleic acid, ribonucleic acid, small interfering ribonucleic acid (siRNA), micro ribonucleic acid (miRNA), messenger ribonucleic acid (mRNA), aptamers/riboswitches, nucleic acid analogues, ribozymes, proteins, enzymes, antibodies, etc.

In a particular embodiment of the invention, a conjugate comprising (1) a nanoparticle comprising a metal oxide, such as, but not limited to, a cerium oxide or an iron oxide, and a nucleobase, and (2) a biologically active agent is provided.

In various embodiments, a conjugate comprising (1) a nanoparticle comprising a metal ion, such as, for example, cerium or iron, or a metal oxide, such as, but not limited to, a cerium oxide or an iron oxide, and a nucleobase, and (2) a biologically active agent comprising, for example, a ribonucleic acid, a deoxyribonucleic acid or a protein, is provided.

In particular embodiments, a conjugate comprising (1) a nanoparticle comprising a metal, such as, for example, cerium or iron, and a nucleobase, and (2) a biologically active agent comprising, for example, small interfering ribonucleic acid (siRNA), micro ribonucleic acid (miRNA) or an aptamer/riboswitch, is provided.

In particular embodiments, a conjugate comprising (1) a nanoparticle comprising a metal oxide, such as, but not limited to, cerium oxide or iron oxide, and a nucleobase, and (2) a biologically active agent comprising, for example, small interfering ribonucleic acid (siRNA), micro ribonucleic acid (miRNA) or an aptamer/riboswitch, is provided.

In a particular embodiment of the invention, a conjugate comprising (1) a nanoparticle comprising a metal, such as, for example, cerium or iron, or a metal oxide, such as, but not limited to, a cerium oxide or an iron oxide, and a nucleobase, and (2) a biologically active agent, is used as a cell transfection agent.

In various embodiments of the invention, a conjugate comprising (1) a nanoparticle comprising a metal, such as, for example, cerium or iron, or a metal oxide, such as, but not limited to, a cerium oxide or an iron oxide, and a nucleobase, and (2) a biologically active agent, are used as a stem-cell promoting factor, a cell reprogramming factor, or a radioprotective factor.

In a particular embodiment of the invention, a process of transfecting a cell, comprising: contacting a cell in an in vitro setting or an in vivo setting with a conjugate comprising 1) a nanoparticle comprising a metal, such as, for example, cerium or iron, or a metal oxide, such as, but not limited to, a cerium oxide or an iron oxide, and a nucleobase, and 2) ribonucleic acid, deoxyribonucleic acid or protein, is provided.

In a particular embodiment of the invention, a process of transfecting a cell, comprising: contacting a cell in an in vitro setting or an in vivo setting with a conjugate comprising 1) a nanoparticle comprising a metal, such as, for example, cerium or iron, or a metal oxide, such as, but not limited to, a cerium oxide or an iron oxide, and a nucleobase, and 2) a small interfering ribonucleic acid, micro ribonucleic acid or an aptamer/riboswitch, is provided.

In a particular embodiment of the invention, a process of transfecting a cell, comprising: contacting a cell in an in vitro setting or an in vivo setting with a conjugate comprising 1) a nanoparticle comprising a metal, such as, for example, cerium or iron, or a metal oxide, such as, but not limited to, a cerium oxide or an iron oxide, and a nucleobase, and 2) a biologically active agent; is provided, wherein said conjugate is used as a stem-cell promoting factor or a cell reprogramming factor.

In particular embodiments, conjugates comprising deoxyribonucleic acid, as described previously, contain plasmid deoxyribonucleic acid.

The invention is further illustrated by the following examples, which are not intended to limit the invention in any manner.

EXPERIMENTAL SECTION

Nanoparticle Scattering and Size Assessments

A simple qualitative characterization of the particle dispersions was performed by assessing the degree of Tyndell scattering exhibited by the dispersions when illuminated by a red laser pen light, relative to the amount of scattering from a sample of the neat solvent.

Quantitative assessments of the particle size of the nanoparticle dispersions were made by a number of techniques.

Dynamic light scattering (DLS) measurements were obtained using a Brookhaven 90Plus Particle Size Analyzer (Brookhaven Instruments Corp., Holtzville, N.Y., U.S.A.) equipped with a quartz cuvette. Samples were typically filtered through a 0.2 micron syringe filter prior to measurement to remove bacterial contaminants. Reported DLS sizes are the lognormal number weighted parameter. These hydrodynamic particle sizes are typically larger than sizes yielded by other techniques because the DLS technique includes contributions from adsorbed ions or molecules that constitute the solvation sphere of the particle.

Particle size estimation by peak-width analysis of X-ray diffraction (XRD) spectra was done using the Scherrer method. Sample preparation for the XRD measurements was done as follows: liquid samples were mixed lightly, placed in a TEFLON boat, allowed to dry under a heat lamp for several hours (until nearly dry), the resulting concentrated liquid was then placed onto a zero background quartz disk, allowed to dry under the heat lamp, and then dried in an oven at either room temperature or at about 80° C. for four hours under a dry nitrogen atmosphere. The coated disk was then analyzed by XRD using a nitrogen gas dry cell attachment. The XRD spectra were recorded on a Rigaku D2000 diffractometer equipped with copper rotating anode, diffraction beam graphite monochrometer tuned to copper K-alpha radiation, and a scintillation detector.

Alternatively, the size of the nanoparticles could be determined by direct analysis of transmission electron microscopy (TEM) images of the particles.

Nanoparticle Charge Assessment

A quantitative assessment of the nanoparticle charge was made by measuring the zeta potential of the nanoparticle dispersions using a Zetasizer Nano ZS from Malvern Instruments (Malvern, Worcestershire, UK).

Examples 1 and 2 include embodiments of the invention employing purine nucleobases (adenine and caffeine).

Preparation of Nanoparticles with Cerium and Adenine

Example 1a 0.4 Molar Ratio of Adenine to Cerium

Into a 400 mL glass beaker containing a magnetic stir bar, 250 mL of high purity (HP) water was introduced, and then 0.629 g of 99% adenine was added with stirring and gradual heating to 40° C. until dissolved. A 5.0 g quantity of $Ce(NO_3)_3.6H_2O$ dissolved in 20 mL HP water was then added to the reaction mixture, resulting in a solution pH of 5.96. Then, a 0.24 g quantity of 50% $H_2O_2$ was diluted into 10 mL of HP water and added to the reaction mixture, which immediately turned an amber red color with a pH of 3.61. After a few minutes of stifling, the reaction mixture turned a translucent tangerine orange color. The reaction mixture was held at 40° C. for 1 hour, and then cooled with stirring overnight, thereby forming a product dispersion at a final pH of 4.55. Particle size analysis by DLS revealed a hydrodynamic particle size of 16.6 nm with a polydispersity of 0.191, indicating that a stable dispersion of nanoparticles had formed.

The product dispersion was then acidified to a pH of about 2.05 by the addition of about 12 mL of 1M $HNO_3$ acid. Acidification led to a particle size increase to a hydrodynamic diameter of 69.65 nm with a polydispersity of 0.1205, as measured by DLS. Upon storage, the acidified mixture lost the transparent tangerine color and turned a turbid pale yellow color.

Example 1b 0.4 Molar Ratio of Adenine to Cerium (Washed)

The procedures of Example 1a were repeated, whereby a product dispersion at a final pH of 4.02 was formed. The product dispersion was then washed by a diafiltration process maintained at a constant volume by addition of about one turnover of HP water, and then concentrated to a final volume of about 100 mL.

Particle size analysis by DLS on the washed/concentrated product dispersion indicated a hydrodynamic diameter of 16.95 nm with a polydispersity of 0.191.

Example 1c 0.6 Molar Ratio of Adenine to Cerium (Washed)

The procedures of Example 1b were repeated except that the amount of adenine was increased to 0.943 g (0.6 molar ratio of adenine to cerium). Following cooling of the reaction mixture, a final pH of 3.85 was obtained. The product dispersion was then washed by a diafiltration process maintained at a constant volume by addition of about one turnover of HP water, and then concentrated to a final volume of about 100 mL.

Particle size analysis by DLS on an aliquot of the washed/concentrated product dispersion indicated a hydrodynamic diameter of 16.5 nm with a polydispersity of 0.166.

Preparation of Nanoparticles with Cerium and Caffeine

Example 2

0.4 Molar Ratio of Caffeine to Cerium

Into a 400 mL glass beaker containing a magnetic stir bar, 250 mL of high purity (HP) water was introduced, and then 0.903 g of 99% caffeine was added with stirring and gradual heating to 40° C. until dissolved. A 5.0 g quantity of $Ce(NO_3)_3.6H_2O$ dissolved in 20 mL HP water was then added to the reaction mixture, resulting in a solution pH of 4.94. Then, a 0.24 g quantity of 50% $H_2O_2$ was diluted into 10 mL of HP water and added to the reaction mixture, which very slowly turned a yellow color and eventually became dark yellow with a pH of 3.66. The reaction mixture was held at 40° C. for 1 hour, and then cooled with stifling over night, thereby forming a product dispersion with the same dark yellow color and transparency at a final pH of 3.75. Particle size analysis by DLS revealed a hydrodynamic particle size of 76.6 nm with a polydispersity of 0.287, indicating that a stable dispersion of nanoparticles had formed.

Examples 3 and 4 include embodiments of the invention employing pyrimidine nucleobases (cytosine and thymine).

Preparation of Nanoparticles with Cerium and Cytosine

Example 3

0.4 Molar Ratio of Cytosine to Cerium

Into a 400 mL glass beaker containing a magnetic stir bar, 250 mL of HP water was introduced, and then 0.517 g of 99% cytosine was added with stirring and gradual heating to 40° C. until dissolved. A 5.0 g quantity of $Ce(NO_3)_3.6H_2O$ was dissolved into 20 mL HP water and then added to the reaction mixture, resulting in a solution pH of 6.37. Then, 0.24 g of 50% $H_2O_2$ was diluted into 10 mL of HP water and added to the reaction mixture. The resulting aqueous solution immediately turned an amber red color with a pH of 3.93. After a few minutes of stirring, the solution turned a translucent tangerine orange color. The reaction mixture was held at 40° C. for 1 hour, and then cooled with stirring over night, thereby forming a product dispersion at a final pH of 4.6. The next day, after stirring and cooling overnight, the solution had remained the same color and transparency.

Particle size analysis by DLS revealed a hydrodynamic particle size of 16.6 nm with a polydispersity of 0.191, indicating that a stable dispersion of nanoparticles had formed in the initial product (labeled Example 3a).

The product dispersion was then acidified to a pH of about 2.05 by the addition of about 12 mL of 1M $HNO_3$ acid. Particle size analysis by DLS revealed a reduction in the hydrodynamic particle size to 9.45 nm with a polydispersity of 0.191 (labeled Example 3b).

The acidified product dispersion was then washed by a diafiltration process maintained at a constant volume by addition of about one turnover of HP water, and then concentrated to a final volume of about 100 mL. Particle size analysis by DLS revealed a similar hydrodynamic particle size of 10.95 nm with a polydispersity of 0.203 (labeled Example 3c).

Preparation of Nanoparticles with Cerium and Thymine

Example 4

0.4 Molar Ratio of Thymine to Cerium

Into a 400 mL glass beaker containing a magnetic stir bar, 250 mL of HP water was introduced, and then 0.587 g of 99% thymine was added with stirring and gradual heating to 40° C. until dissolved. A 5.0 g quantity of $Ce(NO_3)_3.6H_2O$ was dissolved into 20 mL HP water and then added to the reaction mixture, resulting in a solution pH of 4.84. Then, 0.24 g of 50% $H_2O_2$ was diluted into 10 mL of HP water and added to the reaction mixture. The resulting aqueous solution very gradually turned yellow in color with a reduction in pH to 3.82. The reaction mixture was held at 40° C. for 1 hour, and then cooled with stifling over night, thereby forming a product dispersion at a final pH of 3.8. The next day, after stifling and cooling overnight, the solution had remained the same color and transparency.

Particle size analysis by DLS revealed a hydrodynamic particle size of 73.5 nm with a polydispersity of 0.298, indicating that a stable dispersion of nanoparticles had formed. The product dispersion was observed to be stable (no visible change) for several months.

Preparation of Nanoparticles with Cerium and Uracil

Example 5

0.4 Molar Ratio of Uracil to Cerium

Into a 400 mL glass beaker containing a magnetic stir bar, 250 mL of HP water was introduced, and then 0.522 g of 99% uracil was added with stifling and gradual heating to 40° C. until dissolved. A 5.0 g quantity of $Ce(NO_3)_3.6H_2O$ was dissolved into 20 mL HP water and then added to the reaction mixture, resulting in a solution pH of 4.65. Then, 0.24 g of 50% $H_2O_2$ was diluted into 10 mL of HP water and added to the reaction mixture. The resulting aqueous solution very slowly turned yellow in color and eventually became dark yellow along with a reduction in pH to 3.57. The reaction mixture was held at 40° C. for 1 hour, and then cooled with stirring over night, thereby forming a product dispersion at a final pH of 3.6. The next day, after stirring and cooling overnight, the solution had remained the same yellow color and transparency.

Particle size analysis by DLS revealed a hydrodynamic particle size of 96.6 nm with a polydispersity of 0.236, indicating that a stable dispersion of nanoparticles had formed.

Examples 6 and 7 include embodiments of the invention employing 1) a mixture of a purine nucleobase (adenine) and a pyrimidine nucleobase (thymine), and 2) a rare earth metal (cerium) and a transition metal (iron).

Preparation of Nanoparticles with Cerium, Adenine and Thymine

Examples 6a-6b 0.4 Molar Ratio of Adenine and Thymine to Cerium

Into a 400 mL glass beaker containing a magnetic stir bar, 250 mL of HP water was introduced, and then 0.314 g of 99% adenine was added with stirring and gradual heating to 40° C. until dissolved at a pH of 6.92. A 0.293 g quantity of thymine was added to the reaction mixture, which was held at 40° C. until dissolved, thereby forming a solution at pH 7.01. A 5.0 g quantity of $Ce(NO_3)_3.6H_2O$ was dissolved into 20 mL HP water and then added to the reaction mixture, resulting in a solution pH of 5.63. Then, 0.24 g of 50% $H_2O_2$ was diluted into 10 mL of HP water and added to the reaction mixture. The resulting aqueous solution very gradually turned an orange-red color with a reduction in pH to 3.45. The reaction mixture was held at 40° C. for 1 hour, and then cooled with stirring over night, thereby forming an initial product dispersion at a final pH of 3.77 and an ionic conductivity of 10.5 milliSiemens/cm (mS/cm). The next day, after stirring and cooling overnight, the solution had remained the same color and transparency.

Particle size analysis by DLS revealed a hydrodynamic particle size of 17.65 nm with a polydispersity of 0.135, indicating that a stable dispersion of nanoparticles had formed in the initial product dispersion (labeled Example 6a).

The initial product dispersion was then washed by a diafiltration process whereby a constant volume was maintained by addition of about one turnover of HP water, and then concentrated to a final volume of about 100 mL (labeled Example 6b). A decrease in ionic conductivity to 3.44 mS/cm resulted. Particle size analysis by DLS revealed that the washing process had increased the hydrodynamic particle size to 78.45 nm with a polydispersity of 0.114. The washed dispersion assumed a pale yellow color and was observed to be stable (no visible change) for several months.

Examples 6c-6d 0.6 Molar Ratio of Adenine and Thymine to Cerium

Into a 400 mL glass beaker containing a magnetic stir bar, 250 mL of HP water was introduced, and then 0.472 g of 99% adenine was added with stirring and gradual heating to 40° C. until dissolved at a pH of 6.63. A 0.440 g quantity of thymine was added to the reaction mixture, which was held at 40° C. until dissolved, thereby forming a solution at pH 6.40. A 5.0 g quantity of $Ce(NO_3)_3.6H_2O$ was dissolved into 20 mL HP water and then added to the reaction mixture, resulting in a solution pH of 6.10. Then, 0.30 g of 50% $H_2O_2$ was diluted into 10 mL of HP water and added to the reaction mixture. The resulting aqueous solution very gradually turned an orange-red color with a reduction in pH to 4.09. The reaction mixture was held at 40° C. for 1 hour, and then cooled with stirring overnight, thereby forming an initial product dispersion at a final pH of 4.0 and an ionic conductivity of 7.17 mS/cm. The next day, after stirring and cooling overnight, the solution had remained the same color and translucency.

Particle size analysis by DLS revealed a hydrodynamic particle size of 12.0 nm with a polydispersity of 0.295, indicating that a stable dispersion of nanoparticles had formed in the initial product dispersion (labeled Example 6c).

The initial product dispersion was then washed by a diafiltration process whereby a constant volume was maintained by addition of about one turnover of HP water, and then concentrated to a final volume of about 130 mL (labeled Example 6d). A decrease in ionic conductivity to 2.66 mS/cm resulted. Particle size analysis by DLS revealed that the hydrodynamic particle size increased to 17.65 nm with a polydispersity of 0.309 as a result of the washing process. The washed dispersion assumed a pale yellow color and was observed to be stable (no visible change) for several months.

Example 6e-6f 0.8 Molar Ratio of Adenine and Thymine to Cerium

Into a 400 mL glass beaker containing a magnetic stir bar, 250 mL of HP water was introduced, and then 0.629 g of 99% adenine was added with stirring and gradual heating to 40° C. until dissolved at a pH of 6.70. A 0.587 g quantity of thymine was added to the reaction mixture, which was held at 40° C. until dissolved, thereby forming a solution at pH 6.5. A 0.30 g quantity of 50% $H_2O_2$ was diluted into 10 mL of HP water and added to the reaction mixture. Then, a 5.0 g quantity of $Ce(NO_3)_3 \cdot 6H_2O$ was dissolved into 20 mL HP water and added to the reaction mixture. The resulting aqueous solution immediately turned an orange-red color with a reduction in pH to 3.92. The reaction mixture was held at 40° C. for 1 hour, and then cooled with stirring overnight, thereby forming an initial product dispersion at a final pH of 4.08 and an ionic conductivity of 9.6 mS/cm. The next day, after stirring and cooling overnight, the solution had remained the same color and translucency.

Particle size analysis by DLS revealed a hydrodynamic particle size of 13.35 nm with a polydispersity of 0.295, indicating that a stable dispersion of nanoparticles had formed in the initial product dispersion (labeled Example 6e).

The initial product dispersion was then washed by a diafiltration process whereby a constant volume was maintained by addition of about one turnover of HP water, and then concentrated to a final volume of about 100 mL (labeled Example 6f). A decrease in ionic conductivity to 2.54 mS/cm resulted. Particle size analysis by DLS revealed that the hydrodynamic particle size increased to 17.95 nm with a polydispersity of 0.309 as a result of the washing process. The washed dispersion assumed a pale yellow color and was observed to be stable (no visible change) for several months.

Preparation of Nanoparticles with Iron, Adenine and Thymine

Example 7

Equimolar Ratio of Adenine and Thymine to Iron

Into an 800 mL glass beaker containing a magnetic stir bar, 500 mL of HP water was introduced, then 0.676 g of 99% adenine was added with stirring and gradual heating to 40° C. until dissolved, and then 0.631 g of thymine was added and dissolved, forming a solution at pH 7.20. A 4.0 g quantity of $Fe(NO_3)_3 \cdot 9H_2O$ was dissolved into 30 mL HP $H_2O$ and pumped into the reaction mixture under vigorous high shear mixing, resulting in a bright orange colored solution at pH 1.6 Then, 2.4 g of 50% $H_2O_2$ was diluted into 50 mL of HP water and pumped into the reaction mixture. The resulting aqueous solution very gradually turned dark orange-red in color with a pH of 1.7. The reaction mixture was held at 40° C. for 1 hour, and then cooled with stirring overnight, thereby forming a product dispersion (labeled Example 7a) at a final pH of 1.7. The next day, after stirring and cooling overnight, the solution had remained the same color and transparency. A portion of the product dispersion was adjusted to a pH of 3.0 by the addition of ammonium hydroxide (labeled Example 7b).

Particle size analysis by DLS revealed a hydrodynamic particle size of 1.9 nm with a polydispersity of 0.207 for Example 7a (pH 1.7), and particle size of 3.0 nm with a polydispersity of 0.161 for Example 7b (pH 3.0). Thus, stable dispersions of nanoparticles had formed over a range of final pH.

While the invention has been described by reference to various specific embodiments, it should be understood that numerous changes may be made within the spirit and scope of the inventive concepts described. Accordingly, it is intended that the invention not be limited to the described embodiments, but will have full scope defined by claims language.

What is claimed:
1. A process of making nanoparticles, comprising:
    (a) forming a reaction mixture comprising a metal ion, a nucleobase, an oxidant, and water; and
    (b) forming in the reaction mixture a dispersion of nanoparticles.
2. The process according to claim 1, further comprising the step of heating or cooling said reaction mixture to a temperature in the range of about 0° C. to about 100° C.
3. The process according to claim 1, wherein said metal ion comprises cerium or iron.
4. The process according to claim 1, wherein said nanoparticles comprise a metal oxide phase.
5. The process according to claim 4, wherein said metal oxide phase comprises a cerium oxide phase or an iron oxide phase.
6. The process according to claim 1, wherein said nucleobase is a purine.
7. The process according to claim 6, wherein said purine is adenine or caffeine.
8. The process according to claim 1, wherein said nucleobase is a pyrimidine.
9. The process according to claim 8, wherein said pyrimidine is cytosine, thymine or uracil.
10. The process according to claim 1, wherein said nucleobase is a mixture of a purine and a pyrimidine.
11. The process according to claim 10, wherein said mixture comprises adenine and thymine.
12. The process according to claim 1, wherein said oxidant is hydrogen peroxide.

* * * * *